United States Patent
Mueller et al.

(10) Patent No.: US 7,141,211 B2
(45) Date of Patent: Nov. 28, 2006

(54) SYSTEM FOR DETERMINING TOTAL SULFUR CONTENT

(75) Inventors: Friedhelm Mueller, Linkenheim-Hochstetten (DE); Udo Offermanns, Bretten (DE)

(73) Assignee: Siemens Aktiengesellschaft, Munich (DE)

( * ) Notice: Subject to any disclaimer, the term of this patent is extended or adjusted under 35 U.S.C. 154(b) by 135 days.

(21) Appl. No.: 10/347,404

(22) Filed: Jan. 21, 2003

(65) Prior Publication Data

US 2003/0133836 A1     Jul. 17, 2003

Related U.S. Application Data

(63) Continuation of application No. PCT/DE01/02686, filed on Jul. 18, 2001.

(30) Foreign Application Priority Data

Jul. 18, 2000   (DE) ............................ 100 34 879

(51) Int. Cl.
*G01N 31/00*     (2006.01)

(52) U.S. Cl. ................... 422/54; 422/83; 422/89; 422/93; 422/94

(58) Field of Classification Search .......... 422/50, 422/54, 45, 83, 68.1, 78, 82.01, 82.05, 89, 422/90, 91, 94; 436/122, 119, 123, 164
See application file for complete search history.

(56) References Cited

U.S. PATENT DOCUMENTS

| | | | |
|---|---|---|---|
| 3,692,481 A | | 9/1972 | Mitchell |
| 4,054,414 A | * | 10/1977 | Grob et al. ................ 436/115 |
| 4,111,554 A | | 9/1978 | Colin |
| 4,213,763 A | * | 7/1980 | Madec et al. ................ 436/32 |
| 4,293,308 A | | 10/1981 | Sisti |
| 5,049,508 A | | 9/1991 | Hilsher |
| 5,152,963 A | | 10/1992 | Wreyford |
| 6,205,841 B1 | * | 3/2001 | Shibamoto ................ 73/23.41 |

FOREIGN PATENT DOCUMENTS

| | | |
|---|---|---|
| DE | 27 58 470 C2 | 7/1978 |
| DE | 33 06 732 A1 | 8/1984 |
| DE | 37 35 599 A1 | 5/1989 |
| WO | WO 87/07721 | 12/1987 |

* cited by examiner

*Primary Examiner*—Jill Warden
*Assistant Examiner*—Sam P. Siefke
(74) *Attorney, Agent, or Firm*—Sughrue Mion, PLLC

(57) ABSTRACT

In order to determine the total sulfur content of a sample (1), the sample is uniformly combusted with a flame (8). The combustion product sulfur dioxide is fed to a gas chromatograph (15) in which it is separated from other combustion products (9) and is then fed to a detector (17), which is situated downstream and which is provided for determining sulfur dioxide concentration. The combustion of the sample (1) is preferably effected in a flame ionization detector (19), with whose measurement signal (21) the detector signal (20) generated by the detector (17) is freed from signal contents based on non-uniformities of the combustion process.

13 Claims, 2 Drawing Sheets

SYSTEM FOR DETERMINING TOTAL SULFUR CONTENT

This is a Continuation of International Application PCT/DE01/02686, with an international filing date of Jul. 18, 2001, which was published under PCT Article 21(2) in German, and the disclosure of which is incorporated into this application by reference.

FIELD OF AND BACKGROUND OF THE INVENTION

To determine the total sulfur content of a sample to be examined, it is known in the art first to convert the sulfur (sulfur compounds) of the sample either into sulfur dioxide by oxidation or hydrogen sulfide by reduction, i.e. into a compound that is relatively easy to analyze, and subsequently to determine the concentration of the compound by means of a suitable analysis method. For instance, the hydrogen sulfide can be separated from other components of the sample by gas chromatography and can then be readily determined by flame photometry (German Laid-Open Publication 37 35 599 A1). When the sulfur is oxidized, some portion of sulfur trioxide is also formed, in addition to the sulfur dioxide, as a function of the technical combustion conditions. This sulfur trioxide is unsuitable for quantitative determination due to its strong hygroscopic properties. Thus, it is desired to provide technical combustion conditions that cause the sulfur of the sample to be converted into sulfur dioxide to the largest extent possible. This can be achieved, for example, by using catalysts or reactors at temperatures in excess of 1000° C. Over time, however, the surface of the catalyst may become coated with solid particles, e.g., carbon, which are created and deposited during combustion of the sample. It is furthermore difficult to encapsulate the catalyst in such a way that its surface temperature permits use thereof in areas subject to explosion hazards.

OBJECTS OF THE INVENTION

One object of the invention is to enable the determination of total sulfur content of a sample by simple means. A further object is to provide a determination that avoids the aforementioned problems.

SUMMARY OF THE INVENTION

According to one formulation of the invention, these and other objects are attained by a system for determining the total sulfur content of a sample with an enclosed burner to combust the sample in a flame, a downstream feeder to provide a dosed supply of the combustion products, a gas chromatograph to which the combustion products are supplied and which separates the combustion product sulfur dioxide from the remaining combustion products, and a downstream detector to detect the sulfur dioxide.

Combustion of the sample within a closed burner with a small flame makes it possible to comply with explosion protection regulations without incurring additional costs. The burner can be a flame ionization detector, which is frequently used in analytical chemistry and is available in pressure-tight, encapsulated versions for operation in areas subject to explosion hazards. In addition, utilizing a uniform combustion of the sample in a flame that is preferably not too hot, the bound sulfur is largely converted to sulfur dioxide. As a result by subsequently determining the sulfur dioxide concentration by gas chromatography it is possible exactly to determine the total sulfur content of the sample. Moreover, in the system according to the invention, the sample can be burned without being dosed. Only the combustion products are dosed before they are fed to the gas chromatograph. By contrast, in the prior art system using catalysts or reactors, the sample must be dosed prior to combustion because it is technically very difficult, due to the aforementioned problems, among others, to carry out a continuous combustion of the entire sample in the catalyst or reactor.

It has been shown to be advantageous to combust the sample in the burner with a supply of hydrogen and oxygen. Oxygen is preferably supplied as a gas mixture, particularly in the form of air. The latter measure prevents the flame from becoming too hot and sulfur trioxide from being formed during combustion. The hydrogen can be supplied in pure form or as a mixture, e.g., with a carrier gas.

If the sample is a liquid, for instance gasoline, a vaporizer for the sample is preferably inserted in the feed path of the sample in front of the burner, to achieve uniform vaporization and thus undisturbed combustion of the sample. To prevent condensation of the vaporized sample, the feed path of the sample is thermally insulated or arranged in an oven that is maintained within a specified range of temperatures. The oven is provided between the sample vaporizer and the burner, and preferably also encompasses the sample vaporizer. Furthermore, the hydrogen or oxygen (e.g., air) can be supplied to the sample upstream of the sample vaporizer, which has the advantage that the dew point of the vaporized sample is substantially lower due to mixing with the hydrogen or oxygen than it would be without any admixture of gas.

The feed path for the sample preferably includes, at least in sections, a capillary material behind the hydrogen or oxygen feed, e.g., in the form of a wire mesh or fabric, a stranded wire or the like, so that the sample is properly mixed with the supplied gas and does not reach the sample vaporizer in the form of single plugs and does not vaporize irregularly into an inhomogeneous mixture. Moreover, the capillary action of the fabric supports the transport of the liquid sample to the sample vaporizer and inhibits backflow of the vaporized sample. Correspondingly, the interior of the sample vaporizer can be filled with a suitable material to increase its surface area, e.g., a frit.

As previously mentioned, a flame ionization detector can be used as the burner. According to a preferred further embodiment of the invention, the detector function of the flame ionization detector can also be used in such a way that the signal of the detector arranged downstream from the gas chromatograph is corrected with the measuring signal supplied by the flame ionization detector. Quantitative fluctuations in the combustion of the sample, e.g., caused by changes in the density of the sample, influence the measuring signal supplied by the flame ionization detector as well as the detector signal providing the sulfur dioxide concentration, so that by correction, in the simplest case by forming the ratio of the two signals, the detector signal is cleansed of any signal contents caused by irregularities in the combustion process.

To detect the sulfur dioxide at the output of the gas chromatograph, a number of known detectors are available, e.g., a thermal conductivity cell. Particularly simple and highly sensitive detection is afforded by a flame photometer.

BRIEF DESCRIPTION OF THE DRAWINGS

A detailed description of the invention as well as of advantages and preferred embodiments thereof is provided, with reference to the drawing figures in which.

DETAILED DESCRIPTION OF THE PREFERRED EMBODIMENTS

Figure 1:
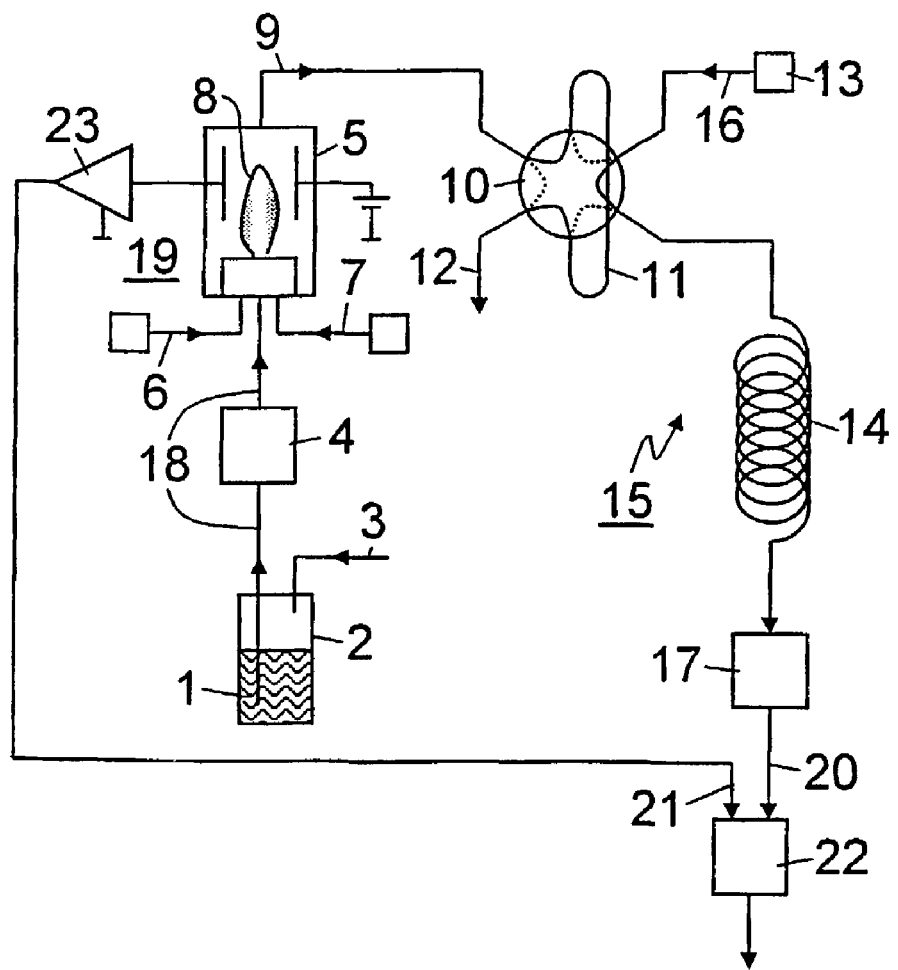
FIG. 1 is an exemplary embodiment of a system according to the invention for determining the total sulfur content of a sample.

A liquid sample 1, which is to be examined for its total sulfur content, e.g. gasoline, is transported from a sample container 2 to a sample vaporizer 4 by means of pressurized gas 3. The vaporized sample 1 is subsequently fed to an enclosed burner 5 where it is combusted in a flame 8 with the supply of hydrogen 6 and air 7. In this process, the sulfur compounds of sample 1 are substantially converted into sulfur dioxide. The gaseous combustion products 9 of the sample 1, i.e. the sulfur dioxide as well as carbon dioxide, water vapor, nitrogen oxides, etc., are fed to a feeder 10, here in the form of a controllable loop valve.

In a first valve position, represented by solid lines, the feeder 10 guides the combustion products 9 through a dosing volume 11 to a gas outlet 12. In addition, in this same valve position, a carrier gas source 13 is connected with a separation device 14 of a gas chromatograph 15, shown here simply as a separation column, so that the separation device 14 is purged by the carrier gas 16. In the second valve position, shown here as a dashed line, the combustion products 9 coming from the burner 5 are guided directly to the gas outlet 12. The dosing volume 11 is then switched into the gas path between the carrier gas source 13 and the separation device 14, so that the carrier gas 16 pushes the combustion products 9 contained in the dosing volume 11 as a plug of gas through the separation device 14. In this process, the sulfur dioxide is separated from the other combustion products and then quantitatively determined in a detector 17. In the embodiment shown, the detector 17 is a flame photo detector (FPD). However, other detectors suitable for detecting sulfur dioxide, e.g., a thermal conductivity detector (TCD), may also be used.

All the parts of the depicted arrangement that carry the combustion products 9 are kept within a temperature range greater than 100° C. to prevent condensation of water vapor, which is one of the combustion products, and to prevent the formation of acids. The area of the feed path 18 for the sample 1 between the sample vaporizer 4 and the burner 5 is likewise heated or thermally insulated so that the vaporized sample 1 cannot condense.

The burner 5 used here is a flame ionization detector (FID) 19, which is frequently used in other contexts of analytical chemistry and which is available in pressure-tight, encapsulated versions for operation in explosive gas atmospheres. In addition, in accordance with the invention, the detector function of the flame ionization detector 19 is used here to provide a correction signal. In particular, the correction signal frees an output signal 20 of the detector 17, arranged downstream of the gas chromatograph 15, of signal contents that are caused by quantitative changes in the sample 1. These quantitative changes distort the measured value of the sulfur dioxide concentration, and thus the total sulfur content measured for the sample 1 derived therefrom. To overcome this problem, the detector signal 20 is corrected, using the measuring signal 21 supplied by the flame ionization detector 19, in a correction device 22, e.g. by forming a ratio. The measuring signal 21 of the flame ionization detector 19 is formed in conventional manner by withdrawing the ions produced in the flame 8 via electrodes under high voltage and by converting the resulting current into the measuring signal 21 in an electrometer amplifier 23.

Figure 2:
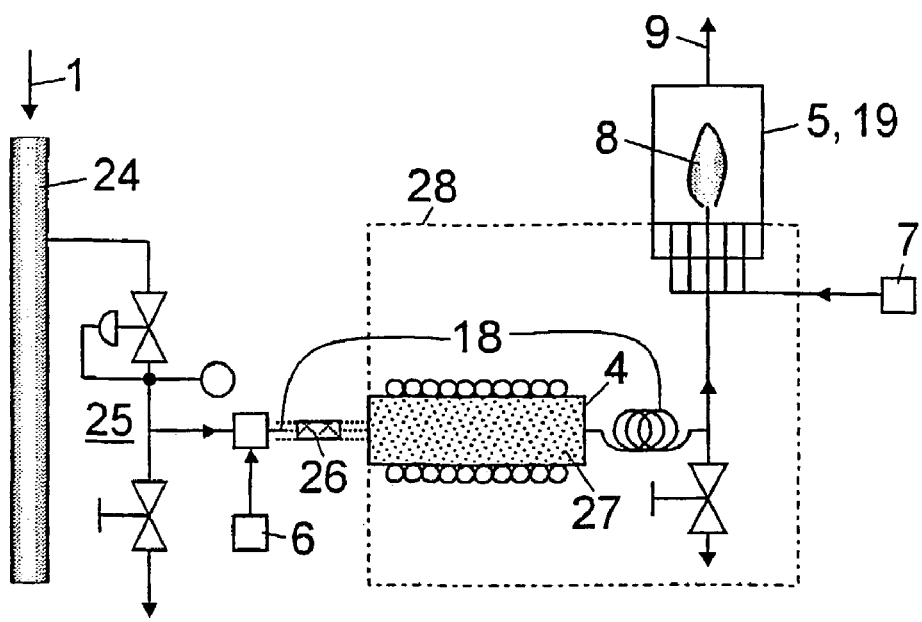
FIG. 2 is an example of continuous vaporization of the sample and its subsequent combustion in a flame.

FIG. 2 shows an example in greater detail of continuous vaporization and subsequent combustion of the liquid sample 1, which in this case flows at a constant pressure through a pipe 24. From the pipe 24, a small amount of the sample is branched off into the feed path (feed line) 18 to the burner 5 (flame ionization detector 19), while the flow rate is kept constant by means of a controllable valve arrangement 25. The sample vaporizer 4 is inserted into the feed path 18. Hydrogen 6 is supplied into the feed path 18 in front of the sample vaporizer 4. The adjacent area of the supply path 18 up to the sample vaporizer 4 contains a capillary material 26, here in the form of a stranded metal wire. This ensures that the sample 1 is properly mixed with the added hydrogen, so that no individual plugs of the sample or hydrogen occur, which could result in irregular vaporization and, thereafter, irregular combustion. In addition, the capillary action of the stranded metal wire enhances the transport of the liquid sample 1 to the sample vaporizer 4 and, vice versa, inhibits backflow of the vaporized sample 1. To achieve uniform vaporization, the interior of the sample vaporizer 4 is filled with a material 27 that has a large surface area, in this case a frit. Mixing with hydrogen causes the dew point of the evaporated sample 1 to be reduced, so that an oven 28 operated at comparatively low temperatures is sufficient to prevent condensation of the vaporized sample 1 or of individual sample components. The continuously vaporized sample 1 mixed with hydrogen finally reaches the burner 5, where it is uniformly combusted in the flame 8 with the addition of air 7.

Figure 3:
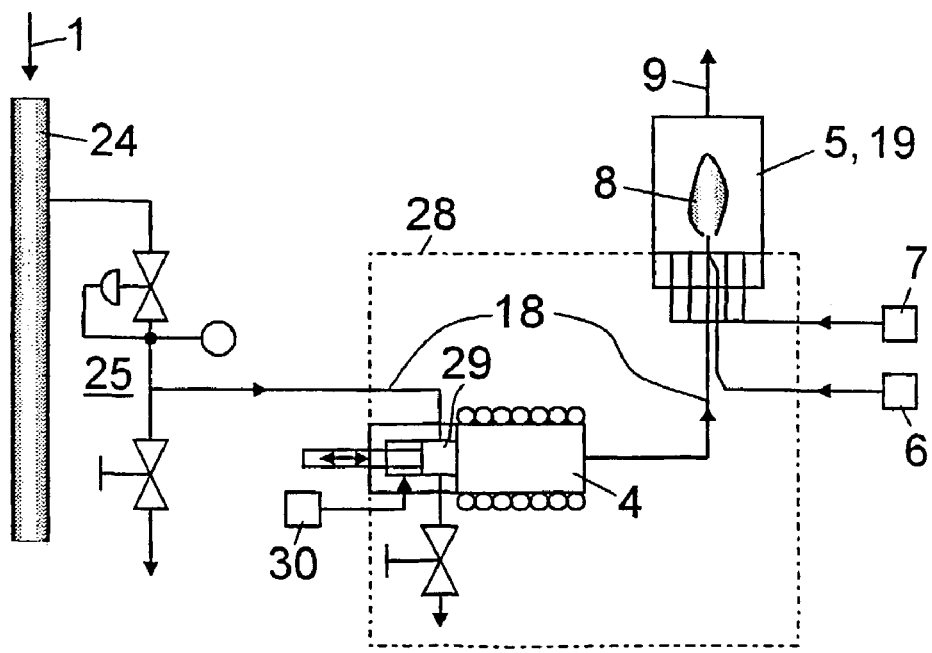
FIG. 3 is an example of discontinuous vaporization of the sample and its subsequent combustion.

In the embodiment shown in FIG. 3, the sample vaporizer 4 is provided with a controllable sample feeder 29, which introduces a predefined volume of liquid sample 1 into the interior of the sample vaporizer 4. After the sample 1 has completely vaporized and has been uniformly distributed in the sample vaporizer 4 and the adjacent section of the feed path 18, it is transported in a continuous stream by means of a carrier gas from a carrier gas source 30 to the burner 5, where it is combusted with the supply of hydrogen 6 and air 7.

In a final preferred embodiment, the sample can instead be injected into the sample vaporizer.

The above description of the preferred embodiments has been given by way of example. From the disclosure given, those skilled in the art will not only understand the present invention and its attendant advantages, but will also find apparent various changes and modifications to the structures and methods disclosed. It is sought, therefore, to cover all such changes and modifications as fall within the spirit and scope of the invention, as defined by the appended claims, and equivalents thereof.

What is claimed is:

1. System for determining the total sulfur content of a sample, comprising:
    an enclosed burner to combust the sample in a flame, wherein the burner is a flame ionization detector supplying a measuring signal,
    a downstream feeder to provide a dosed supply of the combustion products, a gas chromatograph to receive the dosed supply and to separate the combustion product sulfur dioxide from other combustion products, a downstream detector to detect the sulfur dioxide and supply a detector signal, and a correction device correcting the detector signal by the measuring signal supplied by the flame ionization detector.

2. System as claimed in claim 1, further comprising at least one feed path to supply hydrogen and oxygen to the sample for combustion in the burner.

3. System as claimed in claim 2, wherein the oxygen is supplied as air.

4. System as claimed in claim 1, further comprising a liquid-sample vaporizer inserted in a feed path upstream of the burner.

5. System as claimed in claim 4, further comprising an oven for the feed path of the sample at least in an area between the liquid-sample vaporizer and the burner.

6. System as claimed in claim 4, further comprising at least one feed path to supply hydrogen and oxygen to the sample for combustion in the burner, wherein either the hydrogen or the oxygen is fed into the sample upstream of the liquid-sample vaporizer.

7. System as claimed in claim 6, wherein the feed path for the sample contains a capillary material at least in sections downstream of the hydrogen or oxygen supply.

8. System as claimed in claim 5, further comprising at least one feed path to supply hydrogen and oxygen to the sample for combustion in the burner, wherein either the hydrogen or the oxygen is fed into the sample upstream of the liquid-sample vaporizer.

9. System as claimed in claim 8, wherein the feed path for the sample contains a capillary material at least in sections downstream of the hydrogen or oxygen supply.

10. System as claimed in claim 4, wherein an interior of the liquid-sample vaporizer is filled with a high-surface-area material.

11. System as claimed in claim 1, wherein the detector is a flame photometer detector.

12. An apparatus, comprising:

a flame ionization detector combusting a sample into combustion products and supplying a measuring signal indicative of quantitative fluctuations in the sample, a downstream feeder providing a dosed supply of the combustion products, a gas chromatograph receiving the dosed supply and separating the combustion product sulfur dioxide from other combustion products, a downstream detector outputting a detection signal indicative of the separated sulfur dioxide; and a correction device outputting a signal indicative of a total sulfur content of the sample by processing the detection signal and the measuring signal.

13. System for determining the total sulfur content of a sample, comprising:

an enclosed burner to combust the sample in a flame, wherein the burner is a flame ionization detector supplying a measuring signal, a downstream feeder to provide a dosed supply of the combustion products, a gas chromatograph to receive the dosed supply and to separate the combustion product sulfur dioxide from other combustion products, a downstream detector to detect the sulfur dioxide and supply a detector signal;

a correction device correcting the detector signal by the measuring signal supplied by the flame ionization detectors, a liquid-sample vaporizer inserted in a feed path upstream of the burner;

an oven for the feed path of the sample at least in an area between the liquid-sample vaporizer and the burner; and at least one feed path to supply hydrogen and oxygen to the sample for combustion in the burner, wherein either the hydrogen or the oxygen is fed into the sample upstream of the liquid-sample vaporizer, wherein the feed path for the sample contains a capillary material at least in sections downstream of the hydrogen or oxygen supply, and wherein an interior of the liquid-sample vaporizer is filled with a high-surface-area material.

* * * * *